United States Patent [19]

Kraft et al.

[11] 4,409,358

[45] Oct. 11, 1983

[54] COPPER COMPLEXES

[75] Inventors: Helmut Kraft, Wattenheim; Heinz Schumacher, Weinheim; Ernst-Heinrich Pommer; Dietrich Schlotterbeck, both of Limburgerhof; Gregor Ley, Wattenheim, all of Fed. Rep. of Germany

[73] Assignee: BASF Aktiengesellschaft, Fed. Rep. of Germany

[21] Appl. No.: 252,800

[22] Filed: Apr. 10, 1981

[30] Foreign Application Priority Data

May 3, 1980 [DE] Fed. Rep. of Germany ....... 3017123
Jun. 14, 1980 [DE] Fed. Rep. of Germany ....... 3022432
Oct. 18, 1980 [DE] Fed. Rep. of Germany ....... 3039409

[51] Int. Cl.³ .............................................. C07F 1/08
[52] U.S. Cl. .................................................. 524/547
[58] Field of Search ..................... 260/438.1; 524/547; 525/330.2

[56] References Cited

U.S. PATENT DOCUMENTS

| 3,900,504 | 8/1975 | Woerner | 260/438.1 |
| 4,001,400 | 1/1977 | Hager | 424/134 |
| 4,020,180 | 4/1981 | Woerner | 424/294 |
| 4,175,090 | 11/1979 | Berry | 260/438.1 |
| 4,193,993 | 3/1980 | Hilditch | 424/141 |

FOREIGN PATENT DOCUMENTS

| 970321 | 1/1951 | France . |
| 1590623 | 5/1970 | France . |
| 420533 | 12/1934 | United Kingdom . |
| 420589 | 12/1934 | United Kingdom . |
| 593416 | 10/1947 | United Kingdom . |
| 599443 | 3/1948 | United Kingdom . |
| 1411815 | 10/1975 | United Kingdom . |

Primary Examiner—Helen M. S. Sneed
Attorney, Agent, or Firm—Keil & Witherspoon

[57] ABSTRACT

Plant-tolerated copper ammine salts of organic acids, their preparation and their use as crop protection agents.

6 Claims, No Drawings

COPPER COMPLEXES

Copper salts have long been employed in agriculture for the control of fungal diseases of crop plants. To ensure that the copper treatment of the crops remains effective for a lengthy period, sparingly water-soluble, or water-insoluble, inorganic copper salts, for example copper oxychloride, are generally employed. In recent times, oily formulations of copper salts based on low molecular weight organic carboxylic acids have also been disclosed (cf. The Technical Bulletin on Complex-200 from Complex Quimica S.A.); for the same activity, these have a substantially lower copper content than that of the conventional products.

Further, British Pat. No. 1,394,990 has disclosed water-soluble copolymers which are claimed to be produced by polymerizing 20–60 parts of acrylic acid or methacrylic acid, 20–70 parts of an alkyl acrylate or alkyl methacrylate and 5–20 parts of a plasticizing monomer, and in which crop protection agents are to be embedded. The acidic copolymers are also said to be combinable, in the form of their copper salts, with the crop protection agent. However, in our own attempts to repeat the results of this British patent, we did not obtain any useful products.

Finally, German Laid-Open Application DOS No. 2,807,293 and U.S. Pat. No. 3,900,504 discloses copper ammine complexes which have a fungicidal action, but are not suitable for spraying plants since they do not adhere thereto.

We have found simple copper-containing complexes which possess good properties, especially for use in crop protection.

The present invention relates to a crop protection agent which contains a plant-tolerated copper ammine salt of an organic monocarboxylic acid of 4 or more carbon atoms, of a dicarboxylic acid or of a polycarboxylic acid.

The copper is in particular in the form of an ammine complex; the ammonia in the complex can in part also be replaced by low molecular weight volatile amines, such as methylamine. Examples of suitable anions are those of fatty acids of 4 to 20, preferably 5 to 12, carbon atoms, or of polybasic carboxylic acids of up to 12 carbon atoms, preferably dicarboxylic acids of up to 6 carbon atoms.

Interesting examples of such acids are ethylhexanoic acid, fatty acids, such as lauric acid or oleic acid, succinic acid, glutaric acid, adipic acid, benzoic acid, and mixtures of monobasic and/or polybasic carboxylic acids.

Particularly useful anions have proved to be those of polymeric carboxylic acids, for example of polymers prepared from acrylic acid, methacrylic acid and maleic acid and from their copolymers with acrylic acid esters, methacrylic acid esters and/or vinyl compounds, for example vinyl acetate, styrene or vinyl chloride, or from mixtures of the above with one another or with the acids mentioned in the preceding paragraph.

Other comonomers can also be present as copolymerized units in the above polymeric acids, for example complex-forming monomers, eg. acrolein, hydroxypropyl acrylate, butanediol monoacrylate-acetoacetate or vinylimidazole, and/or neutral monomers, eg. acrylamide, methacrylamide or N-methylol methacrylamide, and/or other anionic monomers, eg. acrylamidomethylpropanesulfonic acid and its salts, and/or cationic monomers, eg. dimethylaminoethyl methacrylate or diethylaminoethyl acrylamide, or their quaternized cationic forms.

Mixtures of an aqueous solution of a copper ammine salt and an aqueous solution of the ammonium salt of a polymer which consists of 60–100% of acrylic acid or methacrylic acid and 0–40% of an acrylic acid ester or methacrylic acid ester, as copolymerized units, have proved particularly advantageous.

It is not necessary for the copper ammine salts employed as crop protection agents to be pure.

The novel crop protection agent preferably contains from 0.01 to 10% of copper.

The copper salts according to the invention are most simply prepared by adding ammonia or an amine to an easily soluble copper salt, such as copper(II) sulfate, after which the carboxylic acid is added. They can also be prepared by reacting a copper salt of a weak or volatile acid with the carboxylic acids or polycarboxylic acids, which may or may not have been partially neutralized with ammonia, and then reacting the products with ammonia or aqueous ammonia. The reactants are employed in about the molar ratio. A substantial excess of acid is a disadvantage; an excess of ammonia or amine does not interfere, but if a less than equivalent amount is used, precipitates can form, especially on diluting the product with water to the appropriate use concentrations.

The polymers can be obtained by the conventional methods of mass polymerization, solution polymerization, precipitation polymerization, emulsion polymerization or suspension polymerization.

For example, the monomers can be dissolved, in the absence of oxygen, in a 1:1 mixture of isopropanol and water, to give a 10–50% strength solution. About 0.5–5% (based on the amount of monomers) of a polymerization initiator, for example azo-bis-isobutyronitrile, is added and the mixture is heated for 5 hours at 80° C. The polymers obtained are used, either direct or after isolation, to prepare the novel crop protection agent.

The Examples which follow, and in which all amounts and percentages are by weight, illustrate the invention.

EXAMPLE 1

A solution of 28 parts of ethylhexanoic acid in 25 parts of ethanol, 50 parts of water and 50 parts of concentrated ammonia is added to a stirred solution of 20 parts of $CuSO_4.5H_2O$ in 50 parts of water and 30 parts of concentrated ammonia. A deep blue, clear solution results, which is miscible with water in all proportions. On drying the (dilute) solution at room temperature, a sparingly water-soluble copper compound results.

EXAMPLE 2

A solution of 50 parts of oleic acid in 25 parts of ethanol, 75 parts of water and 50 parts of concentrated ammonia is added to a stirred solution of 20 parts of $CuSO_4.5H_2O$ in 50 parts of water and 30 parts of concentrarted ammonia. The resulting deep blue solution is diluted with water in the ratio of 5 parts of solution to 95 parts of water, giving a milky blue emulsion which over 24 hours shows only slight creaming.

The insoluble copper salt which results on drying is difficult to wet with water.

EXAMPLE 3

A solution of 20 parts of a dicarboxylic acid mixture of about 30% by weight of succinic acid, 40% by weight of glutaric acid and 30% by weight of adipic acid in 40 parts of water and 20 parts of concentrated ammonia is added to a stirred solution of 38 parts of $CuSO_4.5H_2O$ in 75 parts of water and 45 parts of concentrated ammonia.

The resulting deep blue solution gives a clear mixture with water in all proportions. On drying, a water-insoluble copper residue results.

EXAMPLE 4

A solution of 30 parts of $CuSO_4.5H_2O$ in 75 parts of water and 45 parts of concentrated ammonia is added to a stirred solution, in 96.25 parts of water and 3.75 parts of concentrated ammonia, of a solution copolymer which has been obtained from 6.7 parts of methyl acrylate and 13.3 parts of acrylic acid and has a K value of 46. The resulting deep blue clear solution is stable on storage and miscible with water in all proportions. The copper content of the solution is 2.87%.

EXAMPLE 5

The procedure described in Example 4 is followed, except that a solution copolymer obtained from 6.7 parts of ethyl acrylate and 13.3 parts of acrylic acid and having a K value of 42 is used.

EXAMPLE 6

The procedure described in Example 4 is followed, except that a solution copolymer obtained from 6.7 parts of n-butyl acrylate and 13.3 parts of acrylic acid and having a K value of 41 is used.

EXAMPLE 7

37.5 parts of water and 7.5 parts of concentrated ammonia are added to a 50% strength solution, in a 1:1 isopropanol/water mixture, of a copolymer obtained from 25.1 parts of acrylic acid and 12.4 parts of n-butyl acrylate and having a K value of 48. 60 parts of $CuSO_4.5H_2O$ are then dissolved in 50 parts of hot water and when this solution has cooled, 120 parts of concentrated ammonia are added. The solutions obtained are combined. A deep blue, clear solution results, which is stable on storage and is miscible with water in all proportions. The copper content of the solution is 4.36%.

EXAMPLE 8

37.5 parts of water and 3.75 parts of concentrated ammonia are added to a 25% strength solution, in a 1:1 isopropanol/water mixture, of a copolymer obtained from 12.5 parts of acrylic acid and 6.2 parts of n-butyl acrylate and having a K value of 43. 20 parts of $CuSO_4.5H_2O$ are dissolved in 75 parts of hot water. The solution is cooled and 35 parts of concentrated ammonia are added. The solutions obtained are combined. The copper content of the solution is 2.11%.

EXAMPLE 9

A solution of 30 parts of $CuSO_4.5H_2O$ in 60 parts of concentrated ammonia is added to a solution, in 33 parts of water and 10 parts of concentrated ammonia, of a solution polymer obtained from 4.5 parts of acrylic acid and having a K value of 20. The resulting deep blue solution is stable on storage and is miscible with water in all proportions. The copper content of the solution is 5.53%.

EXAMPLE 10

A solution, in 49 parts of water and 10 parts of concentrated ammonia, of a solution polymer obtained from 4.5 parts of acrylic acid and having a K value of about 20 is added dropwise to a solution of 45 parts of $CuSO_4.5H_2O$ in 90 parts of concentrated ammonia. The copper content of the solution is 5.78%.

EXAMPLE 11

A mixture of 10 parts of a 25% strength solution of polymethacrylic acid, having a K value of 60, in propylene glycol, and 10 parts of water is slowly added dropwise to a stirred solution of 15 parts of $CuSO_4.5H_2O$ in 10 parts of water and 40 parts of concentrated aqueous ammonia. A deep blue clear solution is obtained, which is miscible with water in all proportions. On drying the (dilute) solution at room temperature, a sparingly water-soluble copper compound results.

EXAMPLE 12

A mixture of 38 parts of a 40% strength dispersion of an emulsion copolymer of 90% by weight of n-butyl acrylate and 10% by weight of acrylic acid, 40 parts of water and 3 parts of concentrated aqueous ammonia is slowly added dropwise to a solution of 11 parts of $CuSO_4.5H_2O$ in 15 parts of water and 25 parts of concentrated aqueous ammonia. A blue milky cloudy dispersion is obtained, which is miscible with water in all proportions and on drying at room temperature gives a water-resistant film.

EXAMPLE 13

A mixture of 10 parts of a 50% strength solution of a polyacrylic acid, having a K value of 25, 10 parts of concentrated aqueous ammonia and 43 parts of water is slowly added dropwise to a solution of 45 parts of $CuSO_4.5H_2O$ in 90 parts of concentrated aqueous ammonia. The resulting deep blue clear solution is mixed in a ratio of 1:1 with Acronal 567 D plastics dispersion. The resulting blue milky cloudy dispersion is miscible with water in all proportions and, on drying, gives a water-resistant film.

EXAMPLE 14

A solution of 75 parts of a 50% strength solution of a copolymer of 33% by weight of n-butyl acrylate, 65% by weight of acrylic acid and 2% by weight of dimethylaminoethyl methacrylate, which has been quaternized with methyl chloride and has a K value of 48, 37.5 parts of water and 7.5 parts of concentrated aqueous ammonia is added to a stirred solution of 60 parts of $CuSO_4.5H_2O$ in 50 parts of water and 120 parts of concentrated aqueous ammonia. A deep blue solution is obtained, which is stable on storage, is miscible with water in all proportions, and on drying gives a water-resistant residue.

EXAMPLE 15

A mixture of 75 parts of a 25% strength solution of a copolymer of 33% by weight of tert.-butyl acrylate and 67% by weight of acrylic acid, having a K value of 45, 37.5 parts by weight of water and 3.75 parts by weight of concentrated aqueous ammonia is added to a stirred solution of 30 parts of $CuSO_4.5H_2O$ in 75 parts of water and 45 parts of concentrated aqueous ammonia. The resulting deep blue solution is stable on storage, is miscible with water in all proportions, and on drying gives a brittle, water-resistant residue.

EXAMPLE 16

A clear solution of 75 parts of a 25% strength solution of a copolymer of 33% by weight of n-butyl acrylate and 67% by weight of acrylic acid, having a K value of 40, 10 parts of oleic acid, 37.5 parts of water and 25 parts of concentrated aqueous ammonia is added to a stirred solution of 40 parts of $CuSO_4.5H_2O$ in 75 parts of water and 50 parts of concentrated aqueous ammonia. The resulting clear deep blue solution, when diluted with water, gives an adequately stable cloudy spray liquor, which on drying leaves a copper-containing residue which swells in water, but does not dissolve.

EXAMPLE 17

A solution of 75 parts of a 25% strength solution of a copolymer of 33% by weight of styrene and 67% by weight of acrylic acid, having a K value of 36, 37.5 parts of water and 3.75 parts of concentrated aqueous ammonia is added to a stirred solution of 30 parts of $CuSO_4.5H_2O$ in 75 parts of water and 45 parts of aqueous ammonia. The deep blue solution is stable on storage and is miscible with water in all proportions; on drying, a water-resistant residue is left.

EXAMPLE 18

150 parts of a 25% strength aqueous solution of a copolymer of 48% by weight of vinyl imidazole and 52% by weight of acrylic acid, having a K value of 32, is added, with stirring, to 225 parts of a solution of 150 parts of $CuSO_4.5H_2O$ in 200 parts of water and 200 parts of concentrated aqueous ammonia. The resulting dark blue solution is stable on storage and is miscible with water in all proportions.

EXAMPLE 19

A solution of 50 parts of a 25% strength solution of a copolymer of 66% by weight of acrylic acid and 34% by weight of acrolein, having a K value of 32, and 6 parts of concentrated aqueous ammonia is added, with stirring, to 175 parts of a solution of 150 parts of $CuSO_4.5H_2O$ in 400 parts of half-concentrated aqueous ammonia. The resulting solution is stable on storage and miscible with water in all proportions, and, on drying, leaves a water-resistant fungicidal residue.

EXAMPLE 20

A mixture of 100 parts of a 25% strength solution of a copolymer obtained from equal amounts of acrylic acid, maleic anhydride and acrylamidodimethylpropanesulfonic acid and having a K value of 31, 60 parts of water and 20 parts of concentrated aqueous ammonia is added, with stirring, to 180 parts by weight of a solution of 150 parts of $CuSO_4.5H_2O$ in 400 parts of half-concentrated aqueous ammonia. The resulting solution is stable on storage and miscible with water in all proportions, and, on drying, leaves a water-resistant residue.

EXAMPLE 21

A mixture of 50 parts of a 25% strength solution of a copolymer of 50% by weight of acrylic acid, 16% by weight of acrolein, 17% by weight of n-butyl acrylate and 17% by weight of methyl methacrylate, having a K value of 15.5, 100 parts of water and 50 parts of concentrated aqueous ammonia is added to 110 parts of a 27% strength solution of $CuSO_4.5H_2O$ in half-concentrated aqueous ammonia. The resulting solution is stable on storage and miscible with water in all proportions, and, on drying, leaves a water-resistant copper-containing residue.

EXAMPLE 22

A mixture of 100 parts of a 25% strength solution of a copolymer of 90% by weight of acrylic acid and 10% by weight of N-methylol methacrylamide, having a K value of 48, 100 parts of water and 20 parts of concentrated aqueous ammonia is added to 290 parts of a 27% strength solution of $CuSO_4.5H_2O$ in half-concentrated ammonia. The resulting solution is stable on storage and miscible with water in all proportions, and, on drying, leaves a water-resistant residue.

EXAMPLE 23

A mixture of 75 parts of a 25% strength solution of a copolymer of 80% by weight of acrylic acid and 20% by weight of a reaction product of equimolar amounts of hydroxypropyl acrylate and ketene, 37.5 parts by weight of water and 3.75 parts by weight of concentrated aqueous ammonia is added dropwise to a stirred solution of 30 parts of $CuSO_4.5H_2O$ in 75 parts of water and 45 parts of concentrated aqueous ammonia. The resulting solution is stable on storage and miscible with water in all proportions, and, on drying, leaves a water-resistant residue.

EXAMPLE 24

The procedure described in Example 23 is followed, except that in place of the copolymer of acrylic acid and hydroxypropyl acrylate-acetoacetate, a terpolymer of 40% by weight of acrylic acid, 40% by weight of methacrylic acid and 20% by weight of a reaction product of equimolar amounts of hydroxypropyl acrylate and ketene is employed.

If the novel crop protection agent, diluted to the use concentration, is applied to articles, plants or plant parts which are to be treated, the solution, as it dries, leaves a metal poly-salt which is sparingly water-soluble, or water-insoluble, sticks firmly to the article or plant, and retains its fungicidal and/or bactericidal action for a long period.

The novel complexes have, for example, an excellent fungicidal action which suprasses that of the conventional copper-containing fungicides. They an therefore be employed wherever undesired growth of, or infestation by, organisms is encountered. Examples include the inhibition of infestation, by bacteria, algae, fungi, lichen and moss, of plants, building materials, such as natural and artifical stone, flagging, rendering, plaster and paint, and wooden articles exposed to water. In particular, the novel complexes may be used to control *Phytophthora infestans* in tomatoes and potatoes, *Plasmopara viticola* in vines, *Pseudoperonospora humuli* in hops, *Cercospora beticola* in beets, *Cercospora musae* in bananas, *Venturia inaequalis* in apples, *Exobasidium vexans* in tea and *Hemileia vastatrix* in coffee.

Surprisingly, the novel crop protection agents are also excellent bactericides for controlling plant bacterioses. The following are examples of bacterioses which can be controlled with the novel agents: *Corynebacterium michiganense* in tobacco, *Erwinia amylovora* in pears and apples, *Erwinia carotovora* in potatoes, *Pseudomonas lachrymans* in cucumbers, *Pseudomonas phaseolicola* in beans, *Psuedomonas syringae* in lilac,

*Pseudomonas solanacearum* in bananas, *Xanthomonas campestris* in cabbage, *Xanthomonas malvacearum* in cotton and *Xanthomonas oryzae* in rice.

In contrast to the best of the highly active copper compounds, the novel active ingredients, and the agents prepared therewith, are very well tolerated by plants, even in the case of sensitive crops such as pears and apples.

The novel crop protection agents have the further advantage that they can be applied from purely aqueous solution. Hence, their use causes less pollution of the environment than does the treatment with conventional copper compounds.

As a rule, the novel crop protection agents form, after spraying, a coating which sticks firmly to the treated articles or plants. However, if adhesion difficulties arise, a sticker may be added. An example of a suitable sticker is a styrene/n-butyl acrylate dispersion obtainable under the trademark ®Acronal 567 D.

The use formulations of the novel agents can additionally contain other active ingredients, such as herbicides, insecticides, growth regulators or fungicides.

The Examples which follow illustrate the biological action.

EXAMPLE A

Fungicidal activity of the active ingredients of Examples 4–10 on *Phytophthora infestans* in tomatoes Leaves of tomato plants of the Professor Rudloff variety are sprayed with aqueous solutions which contain 0.024, 0.012, 0.006 and 0.003% of copper (calculated as metal). When the spray coating has dried, the leaves are infected with a zoospore suspension of the fungus *Phytophthora infestans*. The plants are then placed in a water vapor-saturated chamber at from 16° to 18° C. After 5 days, the disease has developed sufficiently on the untreated infected control plants for the fungicidal activity of the compounds to be assessed.

The experiment shows that solutions containing about 0.01% of copper very effectively inhibit infection. The fungicides of Examples 3, 6, 7 and 8 prove particularly advantageous.

EXAMPLE B

Bactericidal action on *Erwinia amylovora* in pears (a) Pear trees of the Conference variety, in an area in which the fire blight caused by the *bacterium Erwinia amylovora* is particularly prevalent, were treated at weekly intervals, a total of ten times, with an 0.25% strength solution of the active ingredient from Example 4. Of 40 treated trees, only one showed an area of infection; on the same number of untreated trees, 37 areas of infection were found.

(b) Pear trees were sprayed, in the same manner as described under (a), with an 0.25% strength solution of the active ingredient from Example 5. Areas of infection were found on only 3 out of 40 trees.

There was no visible damage to the trees after treatment.

EXAMPLE C

Plant toleration

Apple seedlings of the Golden Delicious variety, in the 9-leaf stage, were sprayed to run-off with an aqueous solution containing 0.04% of copper (calculated as metal). The test plants were placed in a climatically controlled chamber at 18° C., under additional illumination. 14 days after spraying, the extent of the damage of the plants was assessed.

In this experiment, the Complex 200 formulation produced leaf damage (necroses) at concentrations at which, for example, the compound of Example 5 was satisfactorily tolerated.

We claim:

1. A copper ammine salt of a polymer or copolymer of acrylic acid or methacrylic acid, wherein the term ammine includes complexes of ammonia and/or low molecular weight volatile amines and wherein the anion is a polymer or copolymer of 60–100% of acrylic acid and/or methacrylic acid and 0–40% of a lower alkyl ester of acrylic acid or a lower alkyl ester of methacrylic acid.

2. The copper ammine salt of claim 1, wherein the anion is a copolymer containing acrylic acid and a lower alkyl ester of acrylic acid or methacrylic.

3. The copper ammine salt of claim 1, wherein the anion is a copolymer of methyl acrylate and acrylic acid.

4. The copper ammine salt of claim 1, wherein the anion is a copolymer of ethyl acrylate and acrylic acid.

5. The copper ammine salt of claim 1, wherein the anion is a copolymer of n-butyl acrylate and acrylic acid.

6. An aqueous solution of the copper ammine salt of claim 1.

* * * * *